United States Patent
Mosley

(10) Patent No.: US 10,058,628 B1
(45) Date of Patent: Aug. 28, 2018

(54) TRASH CAN WITH FRAGRANT OIL DISPENSARY

(71) Applicant: Sandra Mosley, Columbia, SC (US)

(72) Inventor: Sandra Mosley, Columbia, SC (US)

( * ) Notice: Subject to any disclaimer, the term of this patent is extended or adjusted under 35 U.S.C. 154(b) by 0 days.

(21) Appl. No.: 15/728,831

(22) Filed: Oct. 10, 2017

(51) Int. Cl.
*B65F 7/00* (2006.01)
*B65F 1/02* (2006.01)
*B65F 1/16* (2006.01)
*A61L 9/04* (2006.01)
*A61L 9/12* (2006.01)

(52) U.S. Cl.
CPC .............. *A61L 9/127* (2013.01); *A61L 9/044* (2013.01); *A61L 9/12* (2013.01); *B65F 1/02* (2013.01); *B65F 1/163* (2013.01); *B65F 2210/129* (2013.01)

(58) Field of Classification Search
CPC ... A61L 9/04; A61L 9/044; A61L 9/12; A61L 9/125; A61L 9/127; B65F 1/02; B65F 1/163; B65F 7/00; B65F 2210/129
USPC ............ 239/34, 37–44, 53, 55–57; 220/87.1, 220/908.2
See application file for complete search history.

(56) References Cited

U.S. PATENT DOCUMENTS

| | | | | |
|---|---|---|---|---|
| 3,008,604 A | * | 11/1961 | Garner | B65F 1/08 206/205 |
| 5,156,290 A | * | 10/1992 | Rodrigues | B65F 1/14 220/366.1 |
| 6,000,571 A | * | 12/1999 | Brooks | B65F 1/06 220/495.04 |
| 6,554,151 B1 | * | 4/2003 | Brennan | B65F 1/06 220/495.04 |
| 7,086,569 B2 | | 8/2006 | Stravitz | |
| 7,273,184 B2 | * | 9/2007 | Brown | A01M 1/2044 220/87.1 |
| 7,516,865 B1 | | 4/2009 | Pierre | |
| 7,878,359 B1 | | 2/2011 | Ko | |
| 8,727,181 B2 | | 5/2014 | Larabee | |
| D716,015 S | | 10/2014 | de Leest | |
| 2006/0081632 A1 | | 4/2006 | Shieh | |
| 2008/0083756 A1 | * | 4/2008 | Daniels | B65F 1/06 220/495.04 |
| 2010/0065570 A1 | * | 3/2010 | Smith | B65F 1/068 220/495.04 |
| 2010/0200670 A1 | | 8/2010 | Tipton | |
| 2011/0226767 A1 | * | 9/2011 | Ekchian | B65F 1/16 220/200 |

(Continued)

FOREIGN PATENT DOCUMENTS

WO 2004063085 A2 7/2004

*Primary Examiner* — Darren W Gorman
(74) *Attorney, Agent, or Firm* — Kyle A. Fletcher, Esq.

(57) ABSTRACT

The trash can with fragrant oil dispensary is a waste container that is configured for use with solid domestic waste. The trash can with fragrant oil dispensary is configured to temporarily store solid domestic waste until the solid domestic waste can be permanently disposed of. The trash can with fragrant oil dispensary further comprises a reservoir, a mesh, and a channel. The reservoir, mesh and channel combine to form fragrance dispensing apparatus. The fragrance dispensing apparatus releases essential oils and other volatile materials to repel insects and to mask objectionable odors. The mesh and the channel attach to the reservoir. The reservoir is attached to an interior surface of the waste container.

16 Claims, 4 Drawing Sheets

(56) References Cited

U.S. PATENT DOCUMENTS

| | | | |
|---|---|---|---|
| 2011/0284544 A1* | 11/2011 | Davies | B65F 1/062 |
| | | | 220/315 |
| 2018/0057255 A1* | 3/2018 | Wright | B65F 1/068 |
| 2018/0057257 A1* | 3/2018 | Campbell | B65F 1/10 |

* cited by examiner

TRASH CAN WITH FRAGRANT OIL DISPENSARY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including deodorization of air, more specifically, a device that deodorizes the air using atomized substances.

SUMMARY OF INVENTION

The trash can with fragrant oil dispensary is a waste container configured for use with solid domestic waste. The trash can with fragrant oil dispensary is configured to temporarily store solid domestic waste until the solid domestic waste can be permanently disposed of. The trash can with fragrant oil dispensary further comprises a reservoir, a mesh, and a channel. The reservoir, mesh and channel combine to form fragrance dispensing apparatus. The fragrance dispensing apparatus releases essential oils and other volatile materials to repel insects and to mask objectionable odors. The mesh and the channel attach to the reservoir. The reservoir is attached to an interior surface of the waste container.

These together with additional objects, features and advantages of the trash can with fragrant oil dispensary will be readily apparent to those of ordinary skill in the art upon reading the following detailed description of the presently preferred, but nonetheless illustrative, embodiments when taken in conjunction with the accompanying drawings.

In this respect, before explaining the current embodiments of the trash can with fragrant oil dispensary in detail, it is to be understood that the trash can with fragrant oil dispensary is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the trash can with fragrant oil dispensary.

It is therefore important that the claims be regarded as including such equivalent construction insofar as they do not depart from the spirit and scope of the trash can with fragrant oil dispensary. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
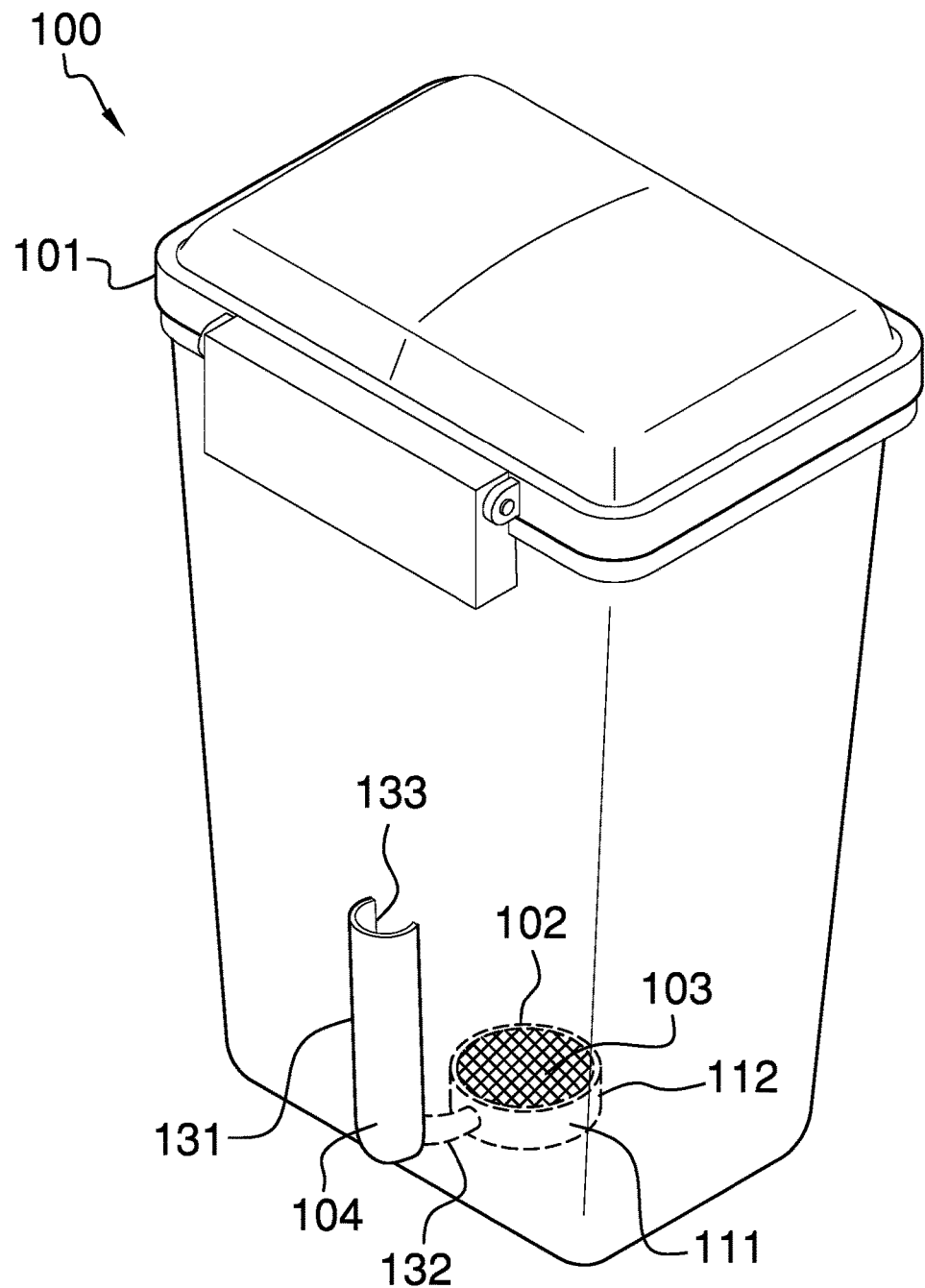
FIG. 1 is a perspective view of an embodiment of the disclosure.
Figure 2:
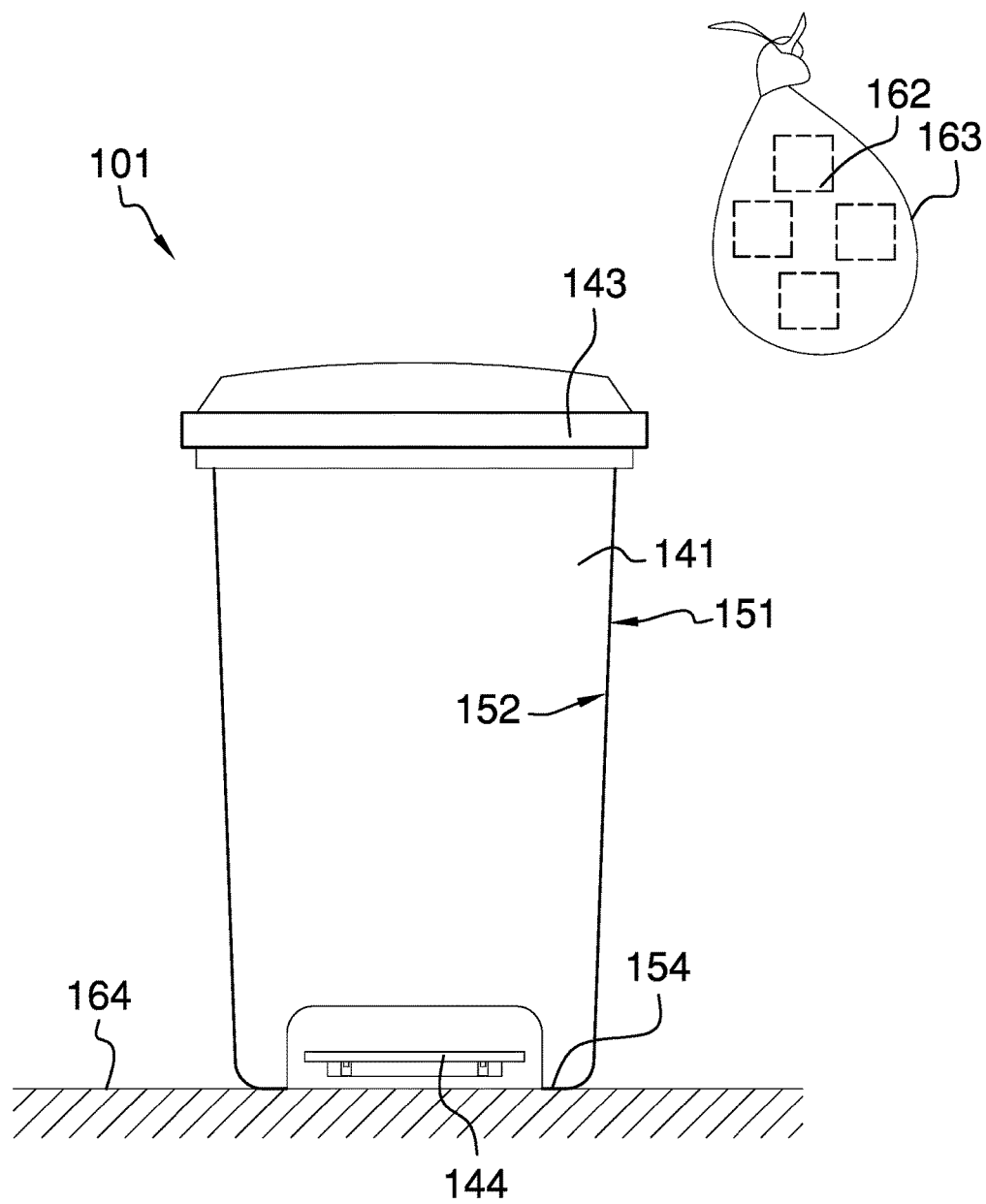
FIG. 2 is a front view of an embodiment of the disclosure.
Figure 3:
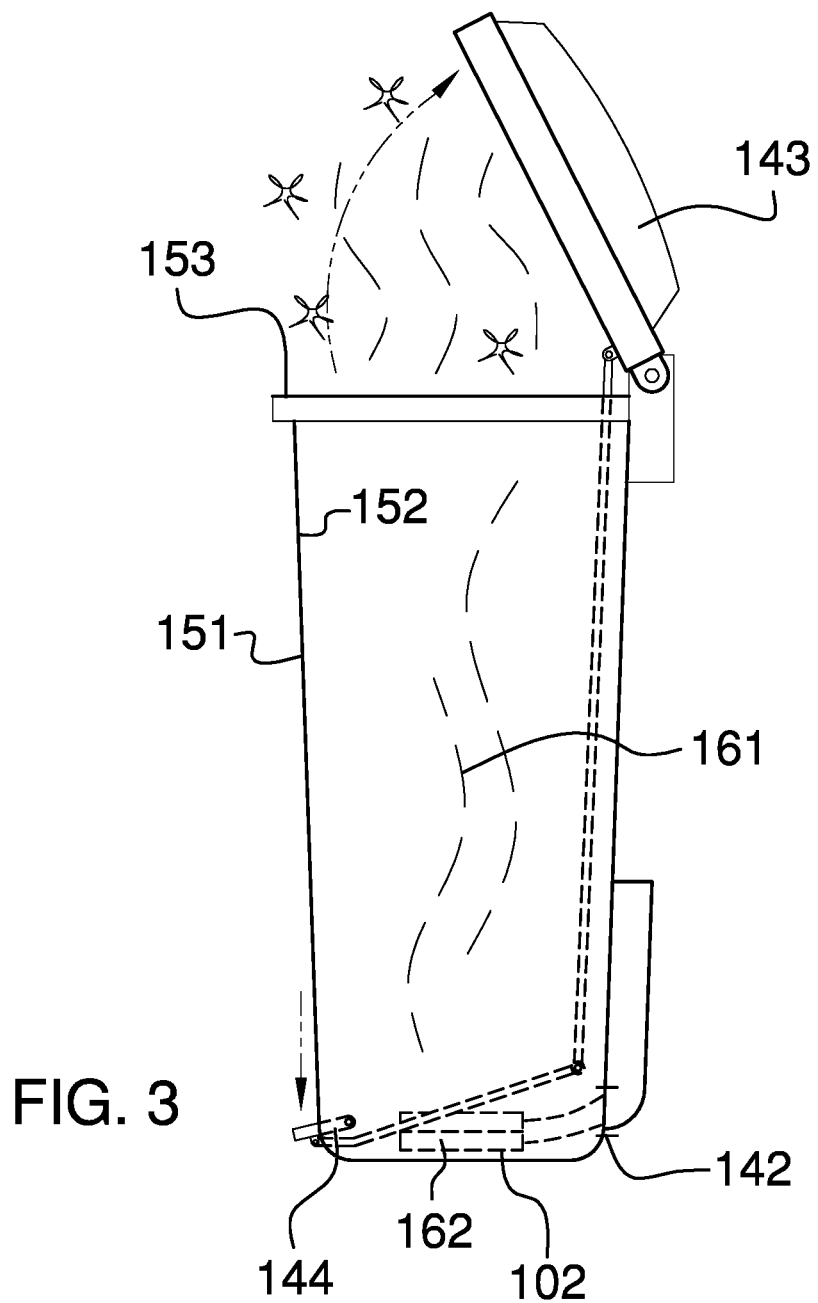
FIG. 3 is a side view of an embodiment of the disclosure.
Figure 4:
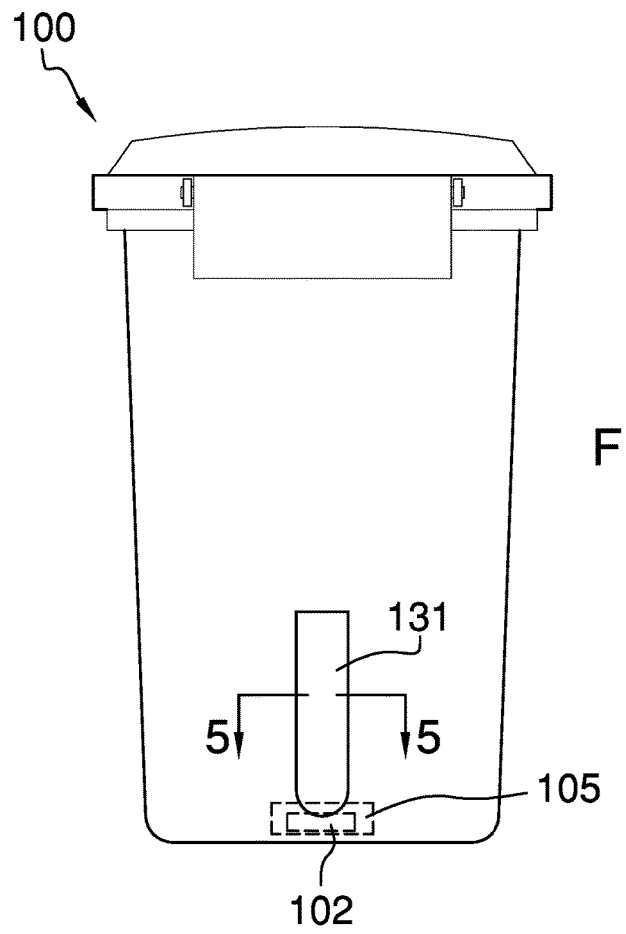
FIG. 4 is a rear view of an embodiment of the disclosure.
Figure 5:
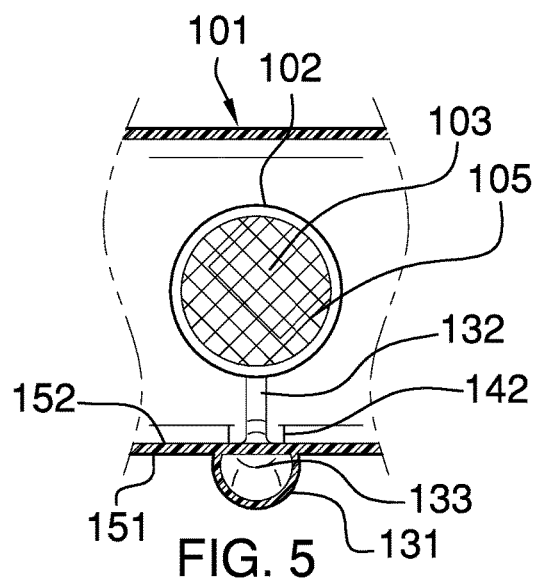
FIG. 5 is a cross-sectional view of an embodiment of the disclosure across 5-5 as shown in FIG. 4.

Detailed reference will now be made to one or more potential embodiments of the disclosure, which are illustrated in FIGS. 1 through 5.

The trash can with fragrant oil dispensary 100 (hereinafter invention) is a waste container 101 configured for use with solid domestic waste 162. The invention 100 comprises a waste container 101, a reservoir 102, a mesh 103, and a channel 104. The invention 100 is configured to temporarily store solid domestic waste 162 to await a more permanent method of disposal. The reservoir 102, mesh 103 and channel 104 combine to form the fragrance dispensing apparatus. The fragrance dispensing apparatus releases essential oils 161 and other volatile materials (hereinafter essential oil 161) to repel insects and to mask objectionable odors. The mesh 103 and the channel 104 attach to the reservoir 102. The reservoir 102 is attached to an interior surface 152 of the waste container 101. The solid domestic waste 162 refers to low-value materials that require disposal.

The essential oil 161 is a customizable mixture of volatile lipids. Examples of an essential oil 161 include, but are not limited to, basil oil, black pepper oil, caraway oil, cannabis flower oil, cedar wood oil, cinnamon oil, citronella oil, chamomile oil, clove oil, davana oil, eucalyptus oil, frankincense oil, horseradish oil, jasmine oil, lavender oil, lemon oil, mandarin, nutmeg, orange oil, oregano oil, peppermint oil, pine oil, sage oil, sandalwood oil, star anise oil, and thyme oil. Basil oil, cedar wood oil, citronella oil, clove oil, lemon oil, peppermint oil, sandalwood oil, and thyme oil are traditionally considered to have insect repellent properties. In the first potential embodiment of the disclosure, the essential oil 161 is a mixture of basil oil, cedar wood oil, lavender oil, lemon oil, sandalwood oil, and thyme oil.

The waste container 101 is a three-dimensional structure that defines a negative space. The negative space formed by the waste container 101 forms the storage location that contains the solid domestic waste 162 stored within the waste container 101. It is preferred that a trash bag 163 line the waste container 101. The trash bag 163 refers to a commercially available liner placed within the waste container 101 to form a barrier between the solid domestic waste 162 and the reservoir 102. The trash bag 163 allows for the easy removal of solid domestic waste 162 from the waste container 101 and prevents the trash bag 163 from contaminating the essential oil 161.

The waste container 101 comprises a storage bin 141, a channel aperture 142, a lid 143, and a foot pedal 144. The storage bin 141 is further defined with an exterior surface 151, an interior surface 152, an access port 153, and a supporting face 154.

The storage bin 141 is the structure that forms the boundaries of the negative space of the waste container 101. The channel aperture 142 is an aperture formed through the wall of the storage bin 141. The lid 143 is a barrier that encloses the access port 153 of the storage bin 141 when access into the waste container 101 is not required. The foot pedal 144 is a foot-operated lever that opens and closes the lid 143 without requiring the use of the hands. Designs and methods to open and close the lid 143 of a waste container 101 using a foot pedal 144 are well-known and documented in the mechanical arts.

The exterior surface 151 refers to the outer surfaces of the boundary formed by the storage bin 141. The interior surface 152 refers to the surfaces of the storage bin 141 that bound the negative space formed by the storage bin 141. The access port 153 refers to an open surface of the storage bin 141 through which solid domestic waste 162 is placed into the waste container 101. The supporting face 154 refers to the face of the storage bin 141 that rests on the supporting surface 164. The access port 153 is the face of the storage bin 141 that is distal from the supporting face 154.

The reservoir 102 is a hollow structure. The reservoir 102 is a storage vessel that contains the essential oil 161 distributed by the invention 100. The essential oil 161 stored within the reservoir 102 evaporates into the negative space formed by the waste container 101. The essential oil 161, or combination of essential oils 161, stored within the reservoir 102 are selected to repel insects from the solid domestic waste 162 and to create a fragrance that masks potentially objectionable odors generated by the solid domestic waste 162. The reservoir 102 comprises a disk shaped well 111 and an open face 112.

The disk shaped well 111 is a capped pipe that forms the physical containment space of the reservoir 102. The closed end of the disk shaped well 111 is placed on the interior surface 152 of the supporting face 154 of the storage bin 141. An adhesive is used to attach the disk shaped well 111 to the interior surface 152 of the supporting face 154 of the storage bin 141.

The open face 112 is the open end of the capped pipe. The open face 112 vents the disk shaped well 111 to the negative space of waste container 101 such that the essential oil 161 evaporates into the negative space of the waste container 101.

The mesh 103 is a metal screen. The metal screen is a commercially available product that is cut to match the open face 112. The mesh 103 attaches to the open face 112 of the reservoir 102. The mesh 103 is a protective structure that accumulated detritus before the detritus can fall into and foul the essential oil 161 contained within the reservoir 102. The perimeter of the mesh 103 is congruent with the perimeter of the open face 112 of the reservoir 102 such that the mesh 103 can be aligned with and placed over the open face 112.

The channel 104 is a structure that transports the essential oil 161 from an externally provided container vessel to the reservoir 102. The channel 104 is accessed from the exterior of the waste container 101. The channel 104 transports the essential oil 161 through the storage bin 141 of the waste container 101 into the reservoir 102. The channel 104 comprises a receiving port 131 and a transfer pipe 132. The receiving port 131 is further defined with a receiving end 133.

The receiving port 131 is a pipe that is attached to the exterior surface 151 of the waste container 101. The essential oil 161 is poured directly into the receiving end 133 of the receiving port 131. The receiving port 131 transports the received essential oil 161 to the transfer pipe 132. The receiving end 133 of the receiving port 131 forms the superior edge of the receiving port 131.

The transfer pipe 132 is a commercially available pipe forms a fluidic connection between receiving port 131 and the disk shaped well 111. The transfer pipe 132 transports the essential oil 161 from the receiving port 131 to the disk shaped well 111. The transfer pipe 132 passes from the exterior of the storage bin 141 to the interior negative space of the storage bin 141 through the channel aperture 142.

The second potential embodiment of the disclosure further comprises a wick 105. The wick 105 is a textile. The wick 105 uses capillary action to draw the essential oil 161 out of the reservoir 102 before the evaporation of the essential oil 161. The wick 105 allows for greater control over the release of the essential oil 161.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Boundary: As used in this disclosure, a boundary refers to a straight or curved line segment that forms: the portion of the perimeter of a first space; and, 2) the portion of the perimeter of a second space. Stated less formally, the boundary forms the delineation between the first space and the second space. When identifying a boundary within this disclosure, a first space will be said to "be bounded" by one or more additional spaces or objects.

Capillary Action: As used in this disclosure, capillary action refers to the tendency of a liquid to experience adhesion forces when exposed to surface or surfaces formed within a narrow structure and the tendency of a liquid to flow as a result of these adhesion force. In the proper circumstances, the adhesive forces of capillary action can overcome gravitational forces or the intermolecular forces that form liquids. The span of the lengths where capillary action predominates is often referred to as a microfluidic scale. On a practical level, the concept of wicking and wicking fabrics rely primarily on capillary action.

Capped Pipe: As used in this disclosure, a capped pipe is a pipe with one closed end and one open end.

Channel: As used in this disclosure, a channel is a tubular passage through which an object or fluid is passed through.

Congruent: As used in this disclosure, congruent is a term that compares a first object to a second object. Specifically, two objects are said to be congruent when: 1) they are geometrically similar; and, 2) the first object can be superimposed over the second object such that the first object aligns, within manufacturing tolerances, with second object.

Correspond: As used in this disclosure, the term correspond means that a first object is in some manner linked to a second object in a one to one relationship.

Detritus: As used in this disclosure, detritus refers to an accumulation of unwanted material on a surface.

Essential Oil: As used in this disclosure, an essential oil is a lipid based solution that contains one or more volatile aroma compounds.

Evaporation: As used in this disclosure, evaporation refers to a phase transition from a liquid phase to a gas.

Exterior: As used in this disclosure, the exterior is used as a relational term that implies that an object is not contained within the boundary of a structure or a space.

Fluid: As used in this disclosure, a fluid refers to a state of matter wherein the matter is capable of flow and takes the shape of a container it is placed within. The term fluid commonly refers to a liquid or a gas.

Fragrance: As used in this disclosure, a fragrance is a distinctive odor that is generally pleasant.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal.

Inferior: As used in this disclosure, the term inferior refers to a directional reference that is parallel to and in the same direction as the force of gravity.

Insect Repellent: As used in this disclosure, an insect repellant is an essential oil wherein the volatile aroma compounds contain an aroma intended to discourage insects from landing on a surface or remaining in an area.

Interior: As used in this disclosure, the interior is used as a relational term that implies that an object is contained within the boundary of a structure or a space.

Lipid: As used in this disclosure, a lipid is an organic molecule that is soluble in nonpolar solvents.

Liquid: As used in this disclosure, a liquid refers to a state of matter that is fluid and that maintains, for a given pressure, a fixed volume that is independent of the volume of the container.

Mesh: As used in this disclosure, the term mesh refers to an openwork fabric made from threads, yarns, cords, wires, or lines that are woven, knotted, or otherwise twisted or intertwined at regular intervals. Synonyms for mesh include net.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set the second set and from the second set to the first set. A one to one fashion means that the one to one relationship exists in only one direction.

Pedal: As used in this disclosure, a pedal is a foot operated lever that is used by the foot to power mechanical devices.

Perimeter: As used in this disclosure, a perimeter is one or more curved or straight lines that bounds an enclosed area on a plane or surface. The perimeter of a circle is commonly referred to as a circumference.

Pipe: As used in this disclosure, the term pipe is used to describe a rigid hollow cylinder used to transport or convey fluids or gases In this disclosure, the terms inner diameter of a pipe and outer diameter are used as they would be used by those skilled in the plumbing arts.

Repellent: As used in this disclosure, a repellent is a chemical substance that is used to repel animals away from an object or location.

Reservoir: As used in this disclosure, a reservoir refers to a container or containment system that is configured to store a liquid.

Strip: As used in this disclosure, the term describes a long and narrow object of uniform thickness that appears thin relative to the length of the object. Strips are often rectangular in shape.

Sublimation: As used in this disclosure, sublimation refers to a phase transition directly from a solid phase to a gas phase in a manner that bypasses the liquid phase.

Superior: As used in this disclosure, the term superior refers to a directional reference that is parallel to and in the opposite direction of the force of gravity.

Supporting Surface: As used in this disclosure, a supporting surface is a horizontal surface upon which an object is placed. Within this disclosure, it is assumed that the object is placed on the supporting surface in an orientation that is appropriate for the normal or anticipated use of the object.

Textile: As used in this disclosure, a textile is a material that is woven, knitted, braided or felted. Synonyms in common usage for this definition include fabric and cloth.

Trash Bag: As used in this disclosure, a trash bag is a disposable bag formed from a sheeting that is used to contain trash and other refuse for in a manner suitable for disposal. Trash bags are often used to line a waste container.

Volatile: As used in this disclosure, volatile refers to a substance that will evaporate or sublimate into a gas state at room temperatures and pressures.

Wick: As used in this disclosure, a wick is a textile material that uses capillary action to draw a liquid out of a reservoir for subsequent use. The use of wicks is well-known and documented in the chemical arts. The process of drawing a liquid through a wick is commonly called wicking.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A deodorizing device comprising:
a waste container, a reservoir, a mesh, and a channel;
wherein the reservoir, the mesh, and the channel attach to the waste container;

wherein the deodorizing device is configured for use with solid domestic waste;

wherein the deodorizing device is configured to store solid domestic waste;

wherein the reservoir, mesh and channel form a fragrance dispensing apparatus;

wherein the fragrance dispensing apparatus releases one or more essential oils;

wherein each of the one or more essential oils is a volatile lipid;

wherein the mesh and the channel attach to the reservoir;

wherein the waste container is a three-dimensional structure that defines a negative space;

wherein the negative space formed by the waste container forms the storage location that contains the solid domestic waste stored within the waste container;

wherein the reservoir is a hollow structure;

wherein the reservoir contains the one or more essential oils;

wherein the one or more essential oils stored within the reservoir evaporates into the negative space formed by the waste container;

wherein the waste container comprises a storage bin and a channel aperture;

wherein the storage bin is further defined with an exterior surface, an interior surface, and a supporting face;

wherein the storage bin is the structure that forms the boundaries of the negative space of the waste container;

wherein the channel aperture is an aperture formed through a wall of the storage bin.

2. The deodorizing device according to claim 1 wherein an access port comprises an opening in the storage bin;

wherein the access port is a face of the storage bin that is distal from the supporting face.

3. The deodorizing device according to claim 2 wherein the reservoir is a disk shaped well;

wherein the disk shaped well is a capped pipe that forms a physical containment space of the reservoir;

wherein the disk shaped well is further defined with an open face and a closed end.

4. The deodorizing device according to claim 3 wherein the closed end of the disk shaped well attaches to an interior surface of the supporting face of the storage bin;

wherein the open face vents the disk shaped well to the negative space of the waste container such that the one or more essential oils evaporates into the negative space of the waste container.

5. The deodorizing device according to claim 4 wherein the mesh is a metal screen;

wherein the mesh attaches to the open face of the reservoir.

6. The deodorizing device according to claim 5 wherein the perimeter of the mesh is congruent with the perimeter of the open face of the reservoir.

7. The deodorizing device according to claim 6 wherein the channel is a structure that transports the one or more essential oils into the reservoir;

wherein the channel is accessed from the exterior of the waste container.

8. The deodorizing device according to claim 7 wherein the channel comprises a receiving port and a transfer pipe;

wherein the receiving port is further defined with a receiving end;

wherein the receiving port is a pipe;

wherein the receiving port transports the received one or more essential oils to the transfer pipe;

wherein the transfer pipe forms a fluidic connection between receiving port and the disk shaped well;

wherein the transfer pipe transports the one or more essential oils from the receiving port to the disk shaped well.

9. The deodorizing device according to claim 8 wherein the receiving port attaches to the exterior surface of the waste container;

wherein the one or more essential oils is poured directly into the receiving end of the receiving port;

wherein the receiving end is the superior structure of the receiving port.

10. The deodorizing device according to claim 9 wherein the transfer pipe passes from the exterior of the storage bin to the interior negative space of the storage bin through the channel aperture.

11. The deodorizing device according to claim 10 wherein the waste container further comprises a lid, and a foot pedal;

wherein the lid is a barrier that encloses the access port of the storage bin;

wherein the foot pedal is a foot operated lever that opens and closes the lid.

12. The deodorizing device according to claim 11 wherein the one or more essential oils comprises a mixture of basil oil, cedar wood oil, lavender oil, lemon oil, sandalwood oil, and thyme oil.

13. The deodorizing device according to claim 10 wherein the deodorizing device further comprises a wick;

wherein the wick is a textile;

wherein the wick uses capillary action to draw the one or more essential oils out of the reservoir before the evaporation of the one or more essential oils.

14. The deodorizing device according to claim 13 wherein the waste container further comprises a lid, and a foot pedal;

wherein the lid is a barrier that encloses the access port of the storage bin;

wherein the foot pedal is a foot operated lever that opens and closes the lid.

15. The deodorizing device according to claim 14 wherein the one or more essential oils comprises a mixture of basil oil, cedar wood oil, lavender oil, lemon oil, sandalwood oil, and thyme oil.

16. The deodorizing device according to claim 14 wherein each of the one or more essential oils is selected from the group consisting of basil oil, black pepper oil, caraway oil, cannabis flower oil, cedar wood oil, cinnamon oil, citronella oil, chamomile oil, clove oil, davana oil, eucalyptus oil, frankincense oil, horseradish oil, jasmine oil, lavender oil, lemon oil, mandarin, nutmeg, orange oil, oregano oil, peppermint oil, pine oil, sage oil, sandalwood oil, star anise oil, and thyme oil.

* * * * *